United States Patent [19]
Raman et al.

[11] Patent Number: 5,368,049
[45] Date of Patent: Nov. 29, 1994

[54] SUPERELASTIC FORMABLE GUIDEWIRE WITH MALLEABLE CLADDING

[75] Inventors: L. Venkata Raman, Framingham, Mass.; Stephen M. Salmon, Sunnyvale, Calif.

[73] Assignee: C. R. Bard, Inc., Murray Hill, N.J.

[21] Appl. No.: 138,554

[22] Filed: Oct. 15, 1993

Related U.S. Application Data

[63] Continuation of Ser. No. 703,419, May 15, 1991, abandoned.

[51] Int. Cl.$^5$ ............................................. A61B 5/00
[52] U.S. Cl. .................................. 128/772; 128/657; 604/281
[58] Field of Search ............... 128/772, 657, 656, 658; 604/95, 164, 280, 281, 282, 264

[56] References Cited

U.S. PATENT DOCUMENTS

| | | |
|---|---|---|
| 3,605,725 | 9/1971 | Bentov . |
| 3,612,038 | 10/1971 | Halligan ............................. 128/658 |
| 3,620,212 | 11/1971 | Fannon et al. . |
| 3,868,956 | 3/1975 | Alfidi et al. . |
| 3,890,977 | 6/1975 | Wilson . |
| 4,248,236 | 2/1981 | Linder ................................ 604/100 |
| 4,345,602 | 8/1982 | Yoshimura et al. . |
| 4,411,655 | 10/1983 | Schreck ............................... 604/165 |
| 4,490,112 | 12/1984 | Tanaka et al. ...................... 433/20 |
| 4,494,833 | 1/1985 | Takamura et al. ................. 351/41 |
| 4,545,390 | 10/1985 | Leary ................................... 128/772 |
| 4,554,929 | 11/1985 | Samson et al. .................... 128/772 |
| 4,665,906 | 5/1987 | Jervis . |

(List continued on next page.)

FOREIGN PATENT DOCUMENTS

| | | |
|---|---|---|
| 0142330 | 5/1985 | European Pat. Off. . |
| 0395098 | 10/1990 | European Pat. Off. . |
| 9013329 | 11/1990 | European Pat. Off. . |
| 0407965 | 1/1991 | European Pat. Off. ............. 128/772 |
| 9100051 | 10/1991 | European Pat. Off. . |
| 2180277 | 7/1990 | Japan .................................. 128/772 |

OTHER PUBLICATIONS

"The Engineering/Design Properties of Nitinol, The 'Metal With A Memory'", *Battelle Memorial Institute*, Columbus Laboratories, Jun. 25, 1969, pp. 1–12.

C. M. Wayman, "Some Applications of S-Memory Alloys", reprinted from *Journal Of Metals*, vol. 32, Jan./1980, pp. 129–137.

K. Otsuka, K. Shimizu, "Pseudoelasticity and Shape Memory Effects in Alloys", *Int'l Metals Review* (1986) vol. 31, No. 3, pp. 93–114.

L. MacDonald Schetky, "Shape-memory Alloys", *Scientific American*, Nov. 1979, vol. 241, No. 5, pp. 74–82.

Otsuka, et al., "Pseudoelasticity In Stress-Induced Martensitic Transformations", *International Quarterly Scientific Reivews Journal*, vol. II, No. 2, pp. 81–172 (P. Feltham, ed. 1977).

*Primary Examiner*—Stephen C. Pellegrino
*Assistant Examiner*—Guy V. Tucker
*Attorney, Agent, or Firm*—Morgan & Finnegan

[57] ABSTRACT

A guidewire is provided having a malleable segment extending beyond a superelastic tip portion of the guidewire. Such a configuration provides a guidewire which is resistant to kinking and plastic deformation in the superelastic portion, but which has a distal segment which can be shaped by a physician immediately prior to use in a surgical procedure. The malleable segment can be attached to the distal end of the superelastic tip portion, or alternatively, can result from a malleable coating on a portion of the superelastic tip, wherein the coating is thick enough to allow the coated portion of the tip to be formed into a desired shape. The malleable segment can be radiopaque to ease fluoroscopic visualization of the guidewire. In addition, the entire guidewire located proximally to the malleable segment can be fabricated from a superelastic alloy to provide resistance to kinking and plastic deformation along virtually the entire length of the guidewire.

21 Claims, 1 Drawing Sheet

U.S. PATENT DOCUMENTS

| | | | |
|---|---|---|---|
| 4,748,986 | 6/1988 | Morrison et al. | 128/772 |
| 4,811,743 | 3/1989 | Stevens | 128/772 |
| 4,827,941 | 5/1989 | Taylor et al. | 128/657 |
| 4,925,445 | 5/1990 | Sakamoto et al. | 604/95 |
| 4,940,062 | 7/1990 | Hampton et al. | 128/772 |
| 4,944,727 | 7/1990 | McCoy | 604/95 |
| 4,966,163 | 10/1990 | Kraus et al. | 128/772 |
| 4,984,581 | 1/1991 | Stice | 128/772 |
| 4,991,602 | 2/1991 | Amplatz et al. | 128/772 |
| 4,998,923 | 3/1991 | Samson et al. | 606/194 |
| 5,003,989 | 4/1991 | Taylor et al. | 128/772 |
| 5,007,434 | 4/1991 | Doyle et al. | 128/772 |
| 5,025,799 | 6/1991 | Wilson | 128/772 |
| 5,060,660 | 10/1991 | Gambale et al. | 128/772 |
| 5,067,489 | 11/1991 | Lind | 128/772 |
| 5,069,226 | 12/1991 | Yamauchi et al. | 128/772 |

SUPERELASTIC FORMABLE GUIDEWIRE WITH MALLEABLE CLADDING

This is a continuation of co-pending application Ser. No. 07/703,419, filed on May 15, 1991, now abandoned.

FIELD OF THE INVENTION

This invention relates to guidewires used in medical procedures.

BACKGROUND OF THE INVENTION

This invention relates to guidewires for use with catheters in blood vessels or other body lumens. For example, such guidewires and catheters commonly are involved in various cardiovascular procedures. More particularly, the invention concerns a guidewire which can be steered into and along body passageways such as a narrow blood vessel (including naturally narrow vessels as well as stenosed vessels) to locate the distal end of the guidewire in a precise position at a target site. Once so placed, a catheter can be advanced over the guidewire directly to the target site. The invention is of particular importance for use in coronary dilatation techniques where the catheter itself is very small in diameter and is difficult to advance and place deeply in the patient's coronary arteries.

A wide variety of guidewires are well known in the prior art. An example of a tapered guidewire having a relatively flexible tip portion and a somewhat more rigid body portion is disclosed in U.S. Pat. No. 4,345,602 to Yoshimura et al. An example of a guidewire for use in coronary angioplasty is described in U.S. Pat. No. 4,545,390 to Leary the teachings of which are incorporated herein, in its entirety, by reference. The Leary patent discloses a small diameter, steerable guidewire, the major portion of which is a flexible, substantially torsionally rigid shaft having a tapered distal portion. The tapered portion is surrounded by a helically wound coil which is attached to the shaft at its proximal and distal ends respectively. Additionally, a portion of the coil extends beyond the distal end of the tapered portion and serves as a highly flexible segment to avoid trauma or damage to a blood vessel through which the guidewire is advanced. The distal tip of the guidewire can be bent to a predetermined shape prior to use by a physician to enhance the steerability of the guidewire.

As described in European Patent Application No. 141,006 to Terumo, conventional prior art guidewires used with catheters commonly include flexible coils formed of wire. In a typical procedure, such a guidewire is inserted percutaneously into a blood vessel, typically using a needle, then the guidewire is manipulated and advanced to a target site. A catheter then is introduced into the blood vessel along and following the path of the guidewire to the target site. Among the difficulties sometimes encountered with conventional guidewires, is the possibility that the distal end of the guidewire may kink as it is advanced through the patient's vasculature. Kinking is the result of a plastic deformation of the guidewire and usually is characterized by a sharp deformation or point bend of the very distal section of the wire. Such a deformation may result from attempting to pass a guidewire through a relatively hard, calcified lesion, a mostly occluded vessel section or a very tortuous vascular section. The wire may kink or bend back upon itself in a condition referred to as prolapse. Thereafter, the wire may return to its original shape, or it may remain permanently deformed if, during the bending, the wire material is bent beyond its elastic limit.

Once kinking occurs, the guidewire is usually discarded because it cannot be adequately straightened for use. Typically that is because of the plastic deformation of the wire or because the physician does not want to spend the time necessary to attempt to straighten the kinked guidewire. Consequently, the procedure may have to be aborted and a new guidewire selected, reinserted, and again manipulated and advanced to the target site. Reinsertion of another guidewire increases the risk of trauma to the blood vessels. Unless great care is taken, the blood vessels can be seriously damaged.

It is important the guidewire be sufficiently flexible so that it does not damage the wall of the blood vessel and so that it can adapt itself to the path of the blood vessel into which it is being inserted.

Additionally, in many instances, it is desirable to provide a guidewire having a curvature or some other shape at its distal end to assist the physician in introducing, advancing and steering the guidewire and catheter to the target site in the blood vessel. However, because of the curvature of the wire, and the resistance of the wire to being straightened when the guidewire is drawn into the catheter and thereafter introduced into the blood vessel, undesirably high friction can occur between the guidewire and catheter. This increases the likelihood of kinking of the guidewire.

It has been suggested that the foregoing difficulties can be addressed by forming guidewires of superelastic alloys. An example of one such guidewire is found in the above-mentioned Terumo European patent application.

Superelastic alloys display a property referred to as stress-induced martensite (SIM). When alloys exhibiting SIM are stressed at a temperature above $M_s$, a temperature denoting the start of martensite transformation, but below the maximum temperature at which martensite formation can occur under stress (denoted $M_d$), they will first deform elastically and then, at a critical stress, begin to transform by the formation of stress-induced martensite. Depending upon whether the temperature is above or below $A_s$, the austenite transformation temperature, the behavior of the material will differ when the deforming stress is released. If the temperature is below $A_s$, the stress-induced martensite is stable; but if the temperature is above $A_s$, the martensite is unstable and will transform back to austenite, with the sample returning or attempting to return to its original shape. This effect is seen in almost all alloys which exhibit a thermoelastic martensitic transformation. However, the extent of the temperature range over which SIM is seen, and the stress and strain ranges for the effect vary greatly with the particular alloy selected. Alloys displaying SIM frequently are referred to as pseudoelastic or superelastic alloys.

One problem with guidewires made of an SIM alloy is that, unlike the conventional prior guidewires, guidewires formed of such alloys cannot be readily formed immediately prior to surgery into a shape desired for a specific procedure. This is because the SIM property which is so desirable in prevention of kinking serves to preclude formability by the physician. Accordingly, there is a need for a guidewire that combines the advantages of guidewires formed of superelastic alloys with the ability to form or shape the distal end of the guidewire immediately prior to use by the physician.

SUMMARY OF THE INVENTION

In accordance with the present invention the guidewire comprises a shaft and a distal end portion wherein the distal end portion contains at least one segment formed of a superelastic alloy having at its distal-most portion a malleable segment which can be formed into a desired shape. The superelastic alloy preferably is a nickel-titanium alloy such as nitinol. In a preferred embodiment, the entire guidewire is fabricated of a superelastic alloy.

In one embodiment, formability is provided to the distal tip of the guidewire by providing a cladding of a malleable material over a portion of the distal end portion, such as over the distal-most tip portion. The malleable cladding extends proximally a short distance and then terminates, thereby leaving the more proximal section of the superelastic distal end portion exposed. The malleable cladding allows the tip of the distal end portion to be bent or formed into a desired curve or shape by a physician immediately prior to use in a surgical procedure. Since the cladding extends only a short distance in the proximal direction, however, the superelastic properties of the distal end portion are maintained over most of the distal end portion of the guidewire.

In a second embodiment, a separate flexible coil or segment is affixed to the distal end of the superelastic material. The coil surrounds a ribbon formed of a malleable material and will retain a shape into which the ribbon is bent. In this embodiment, a cladding of a non-superelastic material is provided on the distal end of the guidewire to serve as an aid for attaching the coil and/or ribbon to the distal end of the superelastic material.

In each embodiment of the invention, the malleable or formable material can be formed of a radiopaque material to aid in fluoroscopic visualization of the distal end of the guidewire during use. Additionally, a lubricious and/or antithrombogenic coating can be applied to the exterior surface of the guidewires described herein for the purpose of minimizing friction on the guidewire and eliminating or minimizing thrombus formation during use of the guidewire. Furthermore, the invention is not limited to guidewires having a superelastic segment only at a distal end portion. Rather, guidewire shafts constructed entirely of superelastic alloys are contemplated for use in the invention as well. Such guidewires would be particularly well-suited for applications in which the lesion is extremely distal, thereby requiring proximal portions of the guidewire to enter tortuous sections of the vascular anatomy.

It also is among the general objects of the invention to provide a guidewire construction which is of a diameter suitable for use with catheters, such as coronary angioplasty catheters, intended to be advanced into small bore arteries.

Another object of the invention is to provide a guidewire which has a high resistance to kinking during use.

Another object of the invention is to provide a guidewire formed at least in part of a superelastic alloy that contains a formable portion at its distal end portion to allow the distal end portion or at least the distal tip of the guidewire to be shaped immediately prior to use in catheterization procedures.

A further object of the invention is to provide a guidewire which presents a reduced risk of trauma to the inner surface of blood vessels.

Another object of the invention is to provide a guidewire suitable for use with balloon dilatation coronary catheters.

Another object of the invention is to provide a superelastic guidewire having a tip portion that can be readily formed to a desired shape.

Still another object of the invention is to provide a superelastic guidewire having a tip segment that is more radiopaque than the portion of the guidewire proximal to the tip.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENTS

Figure 1:
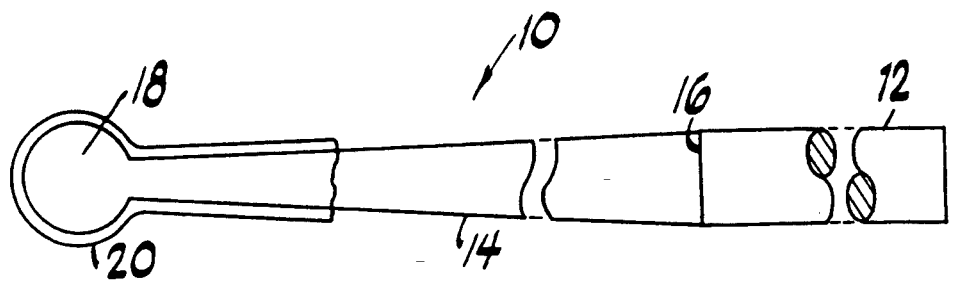
FIG. 1 is a diagrammatic, sectional fragmented illustration of a guidewire of the present invention in which a formable cladding is applied to the distal end of a guidewire having a superelastic tip portion.

FIG. 1 shows the distal portion 10 of one embodiment of a guidewire made in accordance with the present invention. The guidewire comprises a shaft 12 which may be formed from a conventional material such as stainless steel and having a tip portion 14 joined to the distal end of the shaft 12 by any of a variety of well-known methods including brazing, welding and soldering. The tip portion 14 can be ground with, for example, a centerless grinder, to provide it with a gradual taper toward its distal end. A bead 18 such as a tip weld is provided at the distal-most end of the tip portion to enhance the atraumatic character of the tip of the guidewire.

A cladding 20, formed from a malleable material, covers the distal end of the tip portion and extends proximally toward the joint 16 at which the tip portion 14 is attached to shaft 12. The tip portion 14 is constructed of a superelastic alloy, preferably a nickel-titanium alloy such as nitinol. In contrast to the superelastic tip portion, the cladding 20 comprises a layer of a malleable material such as gold that is formed on the superelastic tip portion by any of a variety of well-known electroplating or electroless-plating techniques. Information relating to such plating techniques can be readily obtained from a variety of references including, but not limited to, N. V. Parthasaradhy, "Practical Electroplating Handbook" (Prentice-Hall, Inc. 1989); and the "Metal Finishing" guidebook and directory issues published by Metals & Plastics Publications, Inc. (Hackensack N.J.).

Although extending in the proximal direction, the cladding is terminated at a point located distal to the joint 16, to thereby leave at least a section of superelastic alloy exposed. The cladding is of a thickness sufficient to provide formability to the distal portion of the tip 14 upon which it is present. A lubricious and/or antithrombogenic coating can be applied to the surface of the guidewire to reduce friction on the guidewire during use and to prevent thrombus formation.

The guidewire design embodied in FIG. 1 combines the advantages of both superelastic and conventional guidewires. More specifically, the formable cladding allows a physician to shape the distal tip of the guidewire immediately prior to insertion into a patient, thereby allowing the physician to tailor the tip to a specific procedure or preference, while the superelastic segment of the guidewire provides resistance to the plastic deformation and kinking that may occur in conventional guidewires for the reasons set forth previously.

Additionally, it is not necessary to limit merely the tip portion 14 of the guidewire to a superelastic alloy. Rather, the shaft 12 of the catheter can also be superelastic, thereby providing resistance to kinking and plastic deformation along all but the distal-most, cladding-covered portion of the guidewire. When the shaft 12 of the guidewire is to be fabricated of a superelastic alloy, both the shaft 12 and the tip portion 14 can be formed from a single shaft of a superelastic wire. Such a construction will ease fabrication of the guidewire through the elimination of process steps for attaching the tip portion to the shaft.

The cladding 20 is a malleable, biocompatible material such as gold. Among the requirements for the cladding material are that it be easily applied to the guidewire tip portion, that it provide formability to the superelastic tip at a very low thickness, and preferably that it be radiopaque to enhance fluoroscopic visualization of the guidewire tip. The cladding 20 can be applied using any of a variety of well-known electroplating processes. Additionally, plating techniques other than electroplating can also be used to form the cladding.

In the case of a coronary guidewire such as that depicted in FIG. 1, the outer diameter of the shaft 12 may be of the order of about 0.030 centimeters to 0.047 centimeters. The tip portion 14 is preferably of the order of 32 centimeters long and preferably tapers from a diameter approximating that of the shaft at the joint 16 to a diameter on the order of 0.005 centimeters in the region adjacent to the tip weld or bead 18. The tip weld or bead is preferably of the same diameter as that of the guidewire shaft. The cladding material is applied to a thickness of about 50 microinches and preferably extends proximally from the distal end of the guidewire for a distance of about 2.2 cm. Thus, for a guidewire having a superelastic tip of about 32 cm in length, a section of a superelastic material such as nitinol of approximately 30 cm in length will be exposed between the proximal termination of cladding 20 and the joint 16.

Figure 2:
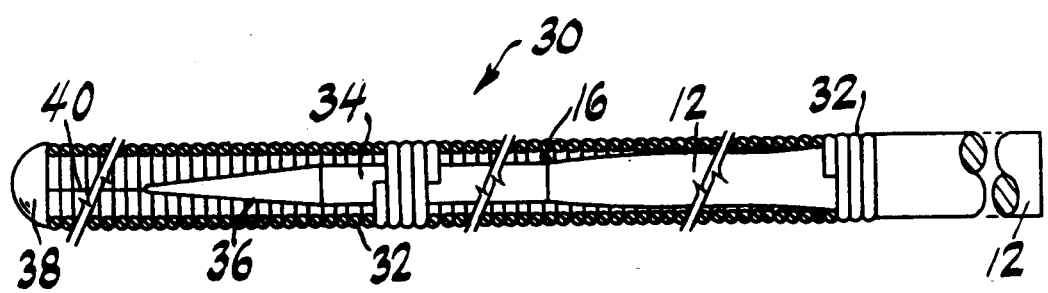
FIG. 2 is a fragmented and sectional illustration of a guidewire of the present invention in which a coil is attached to the distal end of a guidewire having a superelastic tip portion.

FIG. 2 depicts a second embodiment of the guidewire which includes a tip portion formed of a superelastic alloy having a coil attached to the distal end thereof. In FIG. 2, the distal portion of the guidewire 30 comprises a tapered core wire 12 having a tip portion 34 joined to the distal end of core wire 12 at a joint 16. The tip portion 34 can be joined to the core wire 12 using any of a number of methods including welding, brazing and soldering. A cladding 36 of a non-superelastic material covers the distal-most segment of the tip portion 34. As in the previous embodiment, the tip portion 34 is fabricated of a superelastic alloy, preferably a nickel-titanium alloy such as nitinol. Additionally, the tip portion 34 can be gradually tapered toward its distal end.

Attached to the distal end of the superelastic tip portion 34 is a coil 32 which extends both distally and proximally beyond the ends of the tip portion. The coil is essentially a spring that can return to its initial shape subsequent to being bent. Any of a variety of biocompatible materials can be used to form the coil. Among the preferred coil materials are platinum-tungsten alloys, gold-platinum alloys and stainless steel.

The coil includes, at its distal end, a bead 38 to provide a rounded, atraumatic surface at the distal-most end of the guidewire. In addition, a forming ribbon 40 is provided to allow shaping of the coil and to retain the coil if the coil suffers a fracture. The forming ribbon 40 is fabricated of a malleable material such as stainless steel that can be bent to a desired shape by the physician prior to use. Since the coil 32 surrounds the forming ribbon 40 and is readily bent, any shapes formed in the forming wire will be evident in the coil 32 as well. The proximal end of the forming ribbon is attached to the cladding 36, and the distal end of the forming ribbon is attached to the bead 38. Again, brazing, welding or soldering can be used to attach the ends of the forming ribbon to the bead 38 and the cladding 36. As before, a lubricious and/or antithrombogenic coating can be applied to the guidewire to reduce friction on the wire during use and to prevent thrombus formation.

The cladding 36 is applied to the superelastic tip portion 34 to act as a foundation upon which the coil 32 can be attached to the distal end of the tip. The cladding 36 extends a short distance toward the proximal end of the superelastic tip and is terminated at a point distal to the joint 16. The cladding 36 comprises a biocompatible metal or metallic alloy, preferably gold, and serves to provide a surface upon which the proximal end of the coil 32 can be readily brazed, welded or soldered to the superelastic tip 34.

Furthermore, as in the embodiment described previously, the core wire 12 can be fabricated of a superelastic alloy, preferably a nickel-titanium alloy such as nitinol. Such a construction allows the core wire 12 and the tip portion 34 to be fabricated of a single piece of superelastic alloy, thereby eliminating joint 16 and providing the advantages of a superelastic construction to all but the formable coil on the distal end of the guidewire. As set forth previously, a guidewire fabricated entirely of a superelastic alloy with the exception of a malleable distal tip portion would be particularly useful for situations in which the lesion is extremely distal, thereby requiring proximal portions of the guidewire to enter tortuous sections of the vascular anatomy.

For a coronary guidewire of the type depicted in FIG. 2, the outer diameter of the shaft may be of the order of about 0.030 centimeters to 0.041 centimeters. The tip portion is preferably of the order of 30 cm long and preferably tapers to a minimum diameter of approximately 0.005 centimeters. The coil extends approximately 2.2 cm beyond the tip of the guidewire. The outer diameter of the coil is constructed to approximate that of the shaft.

Figure 3:
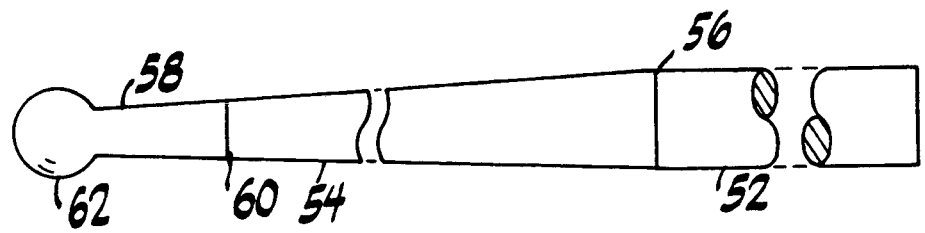
FIG. 3 is a diagrammatic, fragmented, sectional illustration of a guidewire of the present invention in which a solid segment of a formable material is attached to the distal end of a guidewire having a superelastic tip portion and shaft.

FIG. 3 depicts a further variation on the guidewire of the present invention in which the distal-most end of the guidewire comprises a solid segment of a formable material. As set forth previously, in the guidewire depicted in FIG. 3, both the guidewire shaft and tip portion can be fabricated of a superelastic alloy. More specifically, FIG. 3 shows the distal portion of a guidewire 50. The guidewire comprises a shaft 52 which begins a gradual taper at a portion 56 to define a tip region 54. As in the previous embodiments, the superelastic alloy is preferably a nickel-titanium alloy such as nitinol. A malleable segment 58 extends from the distal end of the tip segment 54 and is attached to the tip segment at a joint 60. The malleable segment is constructed of a malleable, biocompatible material and is preferably radiopaque.

A bead 62 such as a tip weld is provided on the distalmost portion of the malleable segment 58 to render the distal end of the guidewire atraumatic. A lubricious and/or antithrombogenic coating can be applied to the guidewire.

In FIG. 3, the shaft 52 is constructed of a superelastic alloy to illustrate one embodiment of the guidewire of the present invention. It is noted that the FIG. 3 guidewire can also be fabricated with a conventional shaft as shown in the earlier embodiments. When so fabricated, portion 56 will comprise a joint between the shaft 52 and the superelastic tip portion 54 as described in the previous embodiments.

As before, for coronary applications the diameter of the shaft 52 may be of the order of 0.030 centimeters to 0.041 centimeters. The tip portion 54 is preferably of the order of 30 cm in length and can taper down to a minimum diameter of approximately 0.005 centimeters at its distal end. The malleable segment 58 extends approximately 2.2 cm beyond the superelastic tip portion 54 and is of approximately the same diameter as the tip portion at joint 60. The bead 62 is approximately the same in diameter as the guidewire core.

Each of the catheters described above comprises a malleable segment located at the distal-most portion of a guidewire to provide a section on the distal end of the guidewire that can be bent or curved into a desired shape by a physician immediately prior to use in a surgical procedure. Additionally, each guidewire comprises at least a segment of a superelastic alloy located proximally to the formable segment to provide at least a portion of the guidewire that is resistant to kinking or plastic deformation. If desired, the entire guidewire located proximally to the formable segment can be constructed of a superelastic alloy to thereby provide a guidewire resistant to plastic deformation or kinking along all, but the final few inches, of its length.

It should be understood that the foregoing description of the present invention is intended to be merely illustrative thereof by way of example and that other equivalents, embodiments and modifications of the invention may be apparent to those skilled in the art.

Having thus described the invention, what I desire to claim and secure by Letters Patent is:

1. A guidewire for a catheter comprising:
   a. a core wire having a distal end portion formed of a superelastic alloy;
   b. a flexible coil surrounding the distal end portion and extending distally beyond the distal end portion; and
   c. a forming ribbon contained within the coil to be formed into a desired shape, the forming ribbon extending between the distal end portion and a portion of the coil located beyond the distal end portion; wherein the distal end portion includes a continuous layer of malleable material on a surface thereof, the malleable material covering at least about 2.2 centimeters of the distal end portion said malleable material being of thickness sufficient to impart manual formability to the distal end portion in the region of the malleable material.

2. A guidewire as in claim 1 wherein the cladding comprises a metal or metallic alloy which does not exhibit superelastic properties.

3. A guidewire as in claim 2 wherein the cladding comprises gold.

4. A guidewire as in claim 1 wherein the superelastic alloy comprises an alloy of nickel and titanium.

5. A guidewire as in claim 4 wherein the superelastic alloy comprises nitinol.

6. A guidewire as in claim 1 wherein the core wire comprises a superelastic metallic alloy.

7. A guidewire as in claim 6 wherein the superelastic alloy comprises an alloy of nickel and titanium.

8. A guidewire as in claim 7 wherein the superelastic alloy comprises nitinol.

9. A guidewire as in claim 6 wherein the distal end portion of the guidewire and the core wire are fabricated from a single segment of a superelastic metallic alloy.

10. A guidewire as in claim 1 wherein the distal end portion of the guidewire is gradually tapered toward the distal end of the guidewire.

11. A guidewire as in claim 1 wherein the coil is fabricated of a material selected from the group consisting of platinum-tungsten alloys, gold-platinum alloys and stainless steel.

12. A guidewire as in claim 1 wherein the coil is formed of a radiopaque material.

13. A guidewire as in claim 1 having a lubricious coating on the surface thereof.

14. A guidewire for a catheter comprising:
   a. a shaft of a superelastic alloy, the shaft defining a body portion, a distal tip portion and a proximal end; and
   b. a continuous layer of malleable material on the surface of the shaft and extending on the distal tip portion at least about 2.2 centimeters and terminating distal to the proximal end, said malleable material being of a thickness sufficient to impart manual formability to the distal tip in the region of the malleable material.

15. A guidewire as in claim 14 wherein the superelastic alloy comprises an alloy of nickel and titanium.

16. A guidewire as in claim 15 wherein the superelastic alloy comprises nitinol.

17. A guidewire as in claim 14 wherein the malleable material comprises gold.

18. A guidewire as in claim 14 wherein the malleable material is radiopaque.

19. A guidewire as in claim 14 additionally comprising a lubricious coating applied to the surface thereof.

20. A guidewire as in claim 14 wherein the distal tip portion is gradually tapered toward the distal end of the guidewire.

21. A guidewire as in claim 20 wherein the distal tip includes a spherical element at its distal end.

* * * * *